United States Patent
Glueck et al.

(10) Patent No.: US 9,132,067 B2
(45) Date of Patent: Sep. 15, 2015

(54) ADHESION PROMOTER BETWEEN OXIDE CERAMIC AND A VENEER MATERIAL, IN PARTICULAR FOR DENTAL PURPOSES, METHOD FOR THE USE THEREOF AND KIT FOR THE PRODUCTION AND APPLICATION THEREOF

(75) Inventors: Olaf Glueck, Echzell (DE); Roland Goebel, Jena (DE)

(73) Assignee: Glueckauf Technologie KG, Echzell (DE)

( * ) Notice: Subject to any disclaimer, the term of this patent is extended or adjusted under 35 U.S.C. 154(b) by 325 days.

(21) Appl. No.: 13/505,670

(22) PCT Filed: Nov. 1, 2010

(86) PCT No.: PCT/DE2010/001262
§ 371 (c)(1),
(2), (4) Date: May 2, 2012

(87) PCT Pub. No.: WO2011/050786
PCT Pub. Date: May 5, 2011

(65) Prior Publication Data
US 2012/0225201 A1    Sep. 6, 2012

(30) Foreign Application Priority Data
Nov. 2, 2009 (DE) .......................... 10 2009 051 593

(51) Int. Cl.
| | | |
|---|---|---|
| A61K 6/00 | (2006.01) | |
| A61K 6/02 | (2006.01) | |
| C03C 8/02 | (2006.01) | |
| C04B 41/45 | (2006.01) | |
| C04B 41/50 | (2006.01) | |
| C04B 37/00 | (2006.01) | |

(52) U.S. Cl.
CPC ............. *A61K 6/0023* (2013.01); *A61K 6/0205* (2013.01); *C03C 8/02* (2013.01); *C04B 37/005* (2013.01); *C04B 41/4535* (2013.01); *C04B 41/50* (2013.01); *C04B 41/502* (2013.01); *C04B 41/5024* (2013.01); *C04B 41/5035* (2013.01); *C04B 2235/3418* (2013.01); *C04B 2235/3472* (2013.01); *C04B 2235/3481* (2013.01); *C04B 2235/96* (2013.01); *C04B 2237/062* (2013.01); *C04B 2237/341* (2013.01); *C04B 2237/343* (2013.01); *C04B 2237/348* (2013.01); *C04B 2237/55* (2013.01)

(58) Field of Classification Search
CPC .... A61K 6/0205; C03C 8/02; C04B 41/4535; C04B 41/50; C04B 41/502; C04B 41/5024; C04B 41/5035
USPC .......................... 106/35, 286.2, 286.8, 286.5
See application file for complete search history.

(56) References Cited

U.S. PATENT DOCUMENTS

| | | | |
|---|---|---|---|
| 4,364,731 A | 12/1982 | Norling et al. | |
| 4,600,390 A | 7/1986 | Goebel et al. | |
| 5,049,190 A | 9/1991 | Goebel et al. | |
| 5,118,296 A * | 6/1992 | Eldred | 433/223 |
| 6,576,173 B1 * | 6/2003 | Koppe et al. | 264/44 |
| 2007/0142498 A1 * | 6/2007 | Brennan et al. | 523/118 |
| 2007/0283850 A1 * | 12/2007 | Kubo et al. | 106/35 |

FOREIGN PATENT DOCUMENTS

| | | | |
|---|---|---|---|
| CN | 101864271 | * | 10/2010 |
| DE | 34 03 894 | | 7/1985 |
| DE | 38 02 043 | | 7/1989 |
| DE | 276 453 | | 2/1990 |
| DE | 10 2005 042 091 | | 3/2007 |
| WO | WO-2007/028787 | | 3/2007 |

OTHER PUBLICATIONS

Eicher, Kappert: Dental Materials and Their Processing, vol. 2, Materials and Their Clinical Processing, Thieme Publishing House, pp. 254-257, Sep. 24, 2008.

* cited by examiner

*Primary Examiner* — Carol M Koslow
(74) *Attorney, Agent, or Firm* — Jordan and Hamburg LLP

(57) ABSTRACT

The aim of the invention is to improve the bond between the oxide ceramic and the veneer material and to increase the durability of said bond. According to the invention, an adhesion promoter (mixture of silicate ceramic and quartz) is applied as a sol to a main body that is to be veneered and that has not yet been densely sintered, the main body being made of oxide ceramic or starting materials thereof. The main body is then sintered to a final state together with the worked-in adhesion promoter, and afterwards the veneer material is applied. The invention is used, for example, to produce dental crowns and bridges having a high load-bearing capacity.

5 Claims, No Drawings

ADHESION PROMOTER BETWEEN OXIDE CERAMIC AND A VENEER MATERIAL, IN PARTICULAR FOR DENTAL PURPOSES, METHOD FOR THE USE THEREOF AND KIT FOR THE PRODUCTION AND APPLICATION THEREOF

BACKGROUND OF THE INVENTION

The invention relates to an adhesion promoter between an oxide ceramic, which has been synthetically produced or is a mixture of natural minerals and consists of one or several metal oxides, in particular zirconium oxide, aluminum oxide or spinel ceramic, and a veneer material, such as silicate ceramic, veneer composites or veneer plastic, that is to be applied onto said oxide ceramic, in particular for dental purposes.

The invention also relates to a method for the use of the adhesion promoter to produce such a composite structure, and to a kit for the production and application of the adhesion promoter.

It is known that oxide ceramics are used to produce dental crowns and bridges having a high load-bearing capacity. For the aesthetic design of such prosthetic frames it is required to apply a tooth-shaded dental ceramic, hereinafter referred to as veneer ceramic (in form of silicate ceramic or also designated as feldspar ceramic or glass ceramic, produced from the main materials feldspar and quartz) on the relatively opaque oxide ceramic surface. Likewise, the veneering material can be a tooth-shaded veneer composite or veneer plastic. In the first step of the procedure, the frame is milled out of a pre-sintered oxide ceramic block by means of diamond-coated instruments. The volume of said frame is about 20% larger than the frame that is to be veneered later. In the subsequent sintering operation (1250° C. to 1600° C.) the frame shrinks to the correct fit. Then, the veneer ceramic is applied to this pre-manufactured and now densely sintered oxide ceramic part and sintered, too (850° C. to 1000° C.). In this process it is intended that the expansion coefficients of the two ceramics are as identical as possible. From a technological point of view the expansion coefficient of the veneer ceramic is slightly smaller than the one of the frame ceramic so that the veneer ceramic is shrunk on the oxide ceramic in a mechanical bond during the sintering and then following cooling processes (e.g. Eichner, Kappert: Dental materials and their processing, Vol. 2, Materials and their clinical processing, Thieme publishing house).

Due to the extreme conditions in the oral environment, the permanent moisture and temperature changes as well as the mechanical load, high tensions are caused exactly at the boundary of both ceramics and as a result the veneer ceramic can directly chip off the surface of the oxide ceramic or the tensions are led into the veneer ceramic so that internal tensions can be produced in it and cause cohesive fractures and thus the chipping in the ceramic.

Because of these numerous problems experts tried to increase the bond strength by a silicate layer on the oxide ceramic and described several methods.

U.S. Pat. No. 4,364,731 A reveals a method in which a layer of silicon dioxide is applied by using a high-frequency magnetron-sputter arrangement.

Another known method (DE 34 03 894 C1) is the application of a silicate layer in a flame hydrolysis process of tetraethoxysilane.

Furthermore, DD 276 453 describes a method in which a silicate chromium oxide layer is applied by a sol-gel solution and then strengthened in a subsequent tempering process (320° C., 2-8 min).

DE 38 02 043 C1 shows a method in which the silicate layer is achieved by a corundum blasting process. Here, a certain amount of silicon dioxide with a mean particle size of <5 µm is added to the blasting corundum. In the impact area of the corundum particles energy densities are locally developed that are sufficient to fuse the fine silicate particles on the surface. All aforementioned efforts are characterized by complex and cost-intensive so equipments and procedures without achieving a real quality leap in the increase of the bond strength and the suppression of the mentioned chipping.

BRIEF DESCRIPTION OF THE INVENTION

The aim of the invention is to improve the bond between the oxide ceramic and the veneer material and to increase the durability of said bond.

According to the invention, the veneer material is not directly applied to the pre-manufactured main body of densely sintered oxide ceramic but first a suitable main body is produced from the not yet densely sintered oxide ceramic or starting materials thereof. For manufacturing reasons, the main body can be pre-sintered at low temperatures but not densely sintered as before. Now, an adhesion promoter is applied as a sol (slip) to the surface of the pre-manufactured main body that is to be veneered and said adhesion promoter diffuses into the surface of the not yet densely sintered main body (up to a depth of 10 µm, depending on the use).

The adhesion promoter consists of a mixture of feldspar and quartz particles in a pure and/or processed form, such as silicate ceramic in the mixing ratio of between 95:05 and 10:90, and of a suitable dispersant (dispersing agent), e.g. water. Another suitable mixing ratio of feldspar to quartz of from 90:10 to 15:85.

After the application of the adhesion promoter the treated surface of the main body is dried (e.g. by the ambient air or by heating) or hardened or polymerized.

Only then, the main body is densely sintered at temperatures ranging from 1250° C. to 1600° C. Thus, the oxide ceramic achieves its full mechanic strength and robustness.

Afterwards, the method known per se is used to apply the veneer material (e.g. silicate ceramic or veneer plastic) on the now densely sintered main body the surface of which, according to the invention, has been penetrated by the adhesion promoter before.

In said sintering process of the oxide ceramic the diffused feldspar and quartz particles are bonded in the oxide ceramic frame. For dental applications, for example a veneer ceramic (feldspar ceramic) applied as a veneer material is also sintered (at temperatures from 850° C. to 1.000° C.). One effect of this process is the formation of the ceramic structures of the veneer ceramic and another effect, which is decisive for the bond, is the production of metal-oxygen-silicon bonds between the firmly anchored metal oxides in the oxide ceramic matrix and the silicate in the feldspar ceramic or the quartz. This reaction guarantees an additional optimal chemical bond between the oxide and veneer ceramic, similar to the bond between dental alloys and veneer ceramic clinically proven during decades.

Surprisingly, not only a stronger bond that can consequently bear higher loads and has a longer durability is produced by the adhesion promoter diffused into the surface of the not yet densely sintered oxide ceramic but our own investigations have also shown that the risk of the so called chipping (cohesive chipping or breaking-out of parts of the veneer material in itself) is reduced. This effect is due to changed mechanical tension ratios in the area of the boundary that are caused by the diffusion of the adhesion promoter into the surface of the not yet densely sintered oxide ceramic. The reason for this may be that the invention does not only produce a mechanical bond between the oxide ceramic and the veneer material as it was done in methods so far but that in this invention the adhesion diffuses into the surface of the oxide ceramic, treated as proposed, up to a depth of 10 μm before the final sintering of the oxide ceramic and thus provides the conditions for an additional bond during the application of the veneer material. The silicate structures diffused in the surface are firmly bonded into the oxide ceramic in the final sintering process thereof. However, this bond is essential at the surface because during the following application of the veneer ceramic also a silicate ceramic is applied that chemically reacts via the Si—O—Si bonds with the near-surface bonded silicate in the sintering process and thus a chemical bond is produced between the oxide ceramic and the veneer ceramic.

The known methods for increasing the bond strength could not produce such chemical bonds and therefore they were restricted to only the mechanical bond strength of the described shrinking. The improved bond between the oxide ceramic and the veneer material has not only an effect if veneer ceramic (silicate ceramic) is used but also if other veneer materials, in particular veneer composites or plastics, are used.

It is possible to provide adhesion promoters of the described type for the prepared sol application. But it could also be useful to produce the adhesion promoter specifically for the individual application. For this purpose, a kit would be helpful that contains the starting materials and, possibly, the equipment and instruments for the application. Such a kit could include, for example:

at least first packaging containing feldspar, which could be processed into a silicate ceramic,
at least second packaging containing quartz,
at least third packaging containing a dispersant, e.g. water,
instruments for mixing the adhesion promoter and/or for its application, and
instructions for handling the kit (production and/or application of the adhesion promoter).

In one embodiment, boxes are used as the first, second and third packaging.

DETAILED DESCRIPTION OF THE INVENTION

The invention will be explained in more detail by virtue of two embodiments:

Example 1

A sol consisting of 7.5 g feldspar, 2.5 g quartz and 100 ml distilled water is applied to an oxide ceramic body (95% $ZrO_2$, 5% $Y_2O_3$) that has been pre-sintered at temperatures ranging from 600° C. to 900° C. and has a size of 2×15×15 mm. A brush is used for applying said sol.

The sol (water with solid particles) diffuses in to the near-surface area of the oxide ceramic. Whereas the feldspar and quartz particles remain there the water is evaporated after 1 min. After the diffusion and drying of the sol the oxide ceramic body is finally sintered at about 1600 C. Afterwards, a coating of 1 mm of the veneer ceramic (Zirox) is applied and sintered in the known manner at a temperature of 930 C.

To be able to measure the strength of the material bond oxide ceramic-veneer ceramic, a plastic cylinder (Ø=5 mm, h=2 mm) is modeled on the veneer ceramic for the test purposes mentioned before. A pressure-shear load is applied to this plastic cylinder and if it reaches a correspondingly high level the plastic cylinder with the veneer ceramic is removed from the oxide ceramic but always in such a way that breakage is caused in the veneer ceramic. A portion of the veneer ceramic remains on the oxide ceramic, the other portion remains on the sheared-off plastic cylinder. The average of the measured bond values was 25 MPa. If the same test is performed at finally sintered oxide ceramic bodies (without sol application) the breakage is characterized by the fact that the veneer ceramic is completely removed from the oxide ceramic and completely located on the sheared-off plastic cylinder. In these comparison cases the average of the measured bond values was 20 MPa.

Example 2

A sol consisting of 5 g feldspar, 5 g quartz and 100 ml distilled water is applied to an oxide ceramic body (95% $ZrO_2$, 5% $Y_2O_3$) that has been pre-sintered at temperatures ranging from 600° C. to 1.000° C. and has a size of 2×15×15 mm. A brush is used for applying said sol.

The sol (water with solid particles) diffuses in to the near-surface area of the oxide ceramic. Whereas the feldspar and quartz particles remain there the water is evaporated after 1 min. After the diffusion and drying of the sol the oxide ceramic body is finally sintered at about 1.450 C. An adhesive silane containing methacryl (Siliseal) is applied to this oxide ceramic body. Said silane is used to repair feldspar breakages with plastic. An optimum chemical bond of the feldspar ceramic and plastic is possible by means of this silane. Afterwards, a plastic cylinder (veneer plastic: sinfony, Ø=5 mm, h=2 mm) is modeled on it. A pressure-shear load is applied on this plastic cylinder and if it reaches a correspondingly high level the plastic cylinder is removed from the oxide ceramic but in such a way that breakage is always caused in the veneer plastic. The average of the measured bond values was 20 MPa. If the same test is performed at finally sintered oxide ceramic bodies (without sol application) an adhesive breakage behavior could always be observed at the oxide ceramic surface. In these comparison cases the average of the measured bond values was 8 MPa.

Due to the inventive proposal, a chemical bond of the oxide ceramic and the veneer ceramic or of the oxide ceramic and the veneer plastic is additionally achieved. Under load breakage is always produced in the weakest element (in this case an adhesion breakage in the veneer ceramic or a cohesion breakage in the veneer plastic), whereas without the inventive method the weakest element of the bond combination is the boundary surface between the oxide-ceramic veneer ceramic, and thus the adhesion breakage is caused there.

The invention claimed is:

1. An adhesion promoter for promoting adhesion between an oxide ceramic comprising at least one metal oxide and a veneer material, the adhesion promoter consisting of a mixture of feldspar and quartz in pure or processed form and a dispersant in a ratio of the feldspar and quartz to the dispersant of from 95:05 to 10:90.

2. The adhesion promoter according to claim 1, wherein the ratio of feldspar to quartz is from 90:10 to 15:85.

3. The adhesion promoter according to claim 1, wherein the oxide ceramic is zirconium oxide, aluminum oxide or spinel ceramic, the veneer material is a silicate ceramic, a veneer composite or plastic, and the dispersant is water.

4. The adhesion promoter according to claim 1, wherein the adhesion promoter is a sol.

5. Kit for producing and applying an adhesion promoter for promoting adhesion between an oxide ceramic comprising at least one metal oxide and a veneer material, consisting of:
- first packaging containing feldspar,
- second packaging containing quartz,
- third packaging containing a dispersant,
- instruments for mixing contents of the first, second and third packaging and applying the mixture to a surface of a body formed of an oxide ceramic to which the veneer material is to be applied, and
- instructions for the use of the kit.

* * * * *